(12) United States Patent
Swanson et al.

(10) Patent No.: US 10,013,529 B1
(45) Date of Patent: Jul. 3, 2018

(54) WORKBENCH FOR INTEGRATING APPLICATIONS

(71) Applicant: ALLSCRIPTS SOFTWARE, LLC, Chicago, IL (US)

(72) Inventors: Art Swanson, Cary, NC (US); Ricky Wayne West, Raleigh, NC (US); Sam Christie, Cary, NC (US); David Potochniak, Raleigh, NC (US)

(73) Assignee: Allscripts Software, LLC, Chicago, IL (US)

( * ) Notice: Subject to any disclaimer, the term of this patent is extended or adjusted under 35 U.S.C. 154(b) by 115 days.

(21) Appl. No.: 13/967,302

(22) Filed: Aug. 14, 2013

Related U.S. Application Data

(60) Provisional application No. 61/683,152, filed on Aug. 14, 2012.

(51) Int. Cl.
*H04L 9/00* (2006.01)
*G16H 10/60* (2018.01)
*G06F 9/46* (2006.01)
*G06F 19/00* (2018.01)
*G06F 21/31* (2013.01)

(52) U.S. Cl.
CPC ............ *G06F 19/322* (2013.01); *G06F 21/31* (2013.01)

(58) Field of Classification Search
CPC ... G06F 21/41; G06F 19/322; G06F 17/30569
USPC ........................................................ 705/2–3
See application file for complete search history.

(56) References Cited

U.S. PATENT DOCUMENTS

| | | | | |
|---|---|---|---|---|
| 2002/0120472 | A1* | 8/2002 | Dvorak | G06F 19/322 705/3 |
| 2004/0128165 | A1* | 7/2004 | Block | G06F 19/322 705/2 |
| 2006/0075224 | A1* | 4/2006 | Tao | G06F 21/121 713/164 |
| 2008/0071577 | A1* | 3/2008 | Highley | G06F 19/322 705/3 |
| 2009/0031004 | A1* | 1/2009 | Yagoda | G06F 17/30873 709/218 |
| 2011/0078708 | A1* | 3/2011 | Dokovski | G06F 9/545 719/329 |

(Continued)

*Primary Examiner* — Joy Chng
(74) *Attorney, Agent, or Firm* — Loza & Loza, LLP; Peter Zura

(57) ABSTRACT

Software configured to interface with multiple other disparate software applications or databases to present a single user interface to a user allows the user to view and modify data from multiple applications and/or databases without having to worry about which application the data comes from. The software provides a user interface which presents to the user seamless integration of data from multiple disparate applications/databases, even though the software may have to continually interface with one or both applications to retrieve, modify, and store data. Exemplary such software comprises workbench software configured to integrate multiple EHR applications and allow for retrieval, presentation, creation, editing, and updating of data from such EHR applications. For example, in one preferred implementation, such software facilitates integration of an ambulatory care solution and an enterprise scale solution so as to allow an organization utilizing an ambulatory care solution to leverage data from an enterprise scale solution.

19 Claims, 14 Drawing Sheets

(56) References Cited

U.S. PATENT DOCUMENTS

2012/0215560 A1* 8/2012 Ofek .................... G06F 19/322
705/3

* cited by examiner

Acute Care EHR

| Patients | Visits |
|---|---|

| Name | SSN | Height | Weight | Blood Type | Age | Gender |
|---|---|---|---|---|---|---|
| John Doe | 111-22-3344 | 5'11" | 175 lbs | A+ | 51 | M |
| Bob Doft | 134-45-9235 | 6'1" | 194 lbs | O+ | 45 | M |
| Jane Dogoeth | 456-12-9999 | 5'1" | 115 lbs | AB- | 32 | F |
| Betsy Drasdell | 452-22-8900 | 5'9" | 136 lbs | O- | 31 | F |
| Keith Drittle | 189-42-7890 | 5'7" | 151 lbs | A+ | 31 | M |
| Tyler Drysdale | 198-77-6264 | 5'8" | 147 lbs | AB+ | 47 | M |

Start | 𝒜 Acute EHR | 12:43 PM 08/14/2012

*FIG. 4*

Patient List

| Name | SSN | Height | Weight | Blood Pheno | Rh | Age | Gender |
|---|---|---|---|---|---|---|---|
| Joe Deckings | 118-22-3644 | 68" | 235 lbs | AB | + | 41 | M |
| Bill Dee | 174-45-4512 | 72" | 210 lbs | O | + | 45 | M |
| John Doe | 111-22-3344 | 71" | 175 lbs | A | + | 51 | M |
| Judy Duck | 432-27-8970 | 67" | 116 lbs | A | - | 36 | F |
| Kevin Ducci | 187-43-7850 | 67" | 173 lbs | A | - | 25 | M |
| Ryan Dukakis | 197-74-6274 | 70" | 180 lbs | AB | + | 34 | M |

Prev    Next

Start    A Acute EHR    ♂ Amb. EHR    Ambulatory Care EHR    12:45 PM 08/14/2012

*FIG. 6*

Workbench

Databases: ☑ Acute   ☑ Ambulatory

Welcome Back John Smith | My Account | Logout

| Name | SSN | Ht | Wt | Blood | Age | Gender |
|---|---|---|---|---|---|---|
| Joe Deckings | 118-22-3644 | 5'8" | 235 lbs | AB+ | 41 | M |
| Bill Dee | 174-45-4512 | 6' | 210 lbs | O+ | 45 | M |
| John Doe | 111-22-3344 | 5'11" | 175 lbs | A+ | 51 | M |
| Bob Doft | 134-45-9235 | 6'1" | 194 lbs | O+ | 45 | M |
| Jane Dogoeth | 456-12-9999 | 5'1" | 115 lbs | AB- | 32 | F |
| Betsy Drasdell | 452-22-8900 | 5'9" | 136 lbs | O- | 31 | F |
| Keith Drittle | 189-42-7890 | 5'7" | 151 lbs | A+ | 31 | M |

Start | W Workbench                                                 12:42 PM 08/14/2012

*FIG. 12*

| Databases: | | | Workbench | | | | | — □ ✕ |
|---|---|---|---|---|---|---|---|---|
| | | | Welcome Back John Smith \| My Account \| Logout | | | | | |
| | ☑ Acute | ☑ Ambulatory | | | | Search | | |
| Name | SSN | Ht | Wt | Blood | Age | Gender | | |
| Joe Deckings | 118-22-3644 | 5'8" | 235 lbs | AB+ | 41 | M | | |
| Bill Dee | 174-45-4512 | 6' | 210 lbs | O+ | 45 | M | | |
| John Doe | 111-22-3344 | 5'11" | 181 lbs | A+ | 51 | M | | |
| Bob Doft | 134-45-9235 | 6'1" | 194 lbs | O+ | 45 | M | | |
| Jane Dogoeth | 456-12-9999 | 5'1" | 115 lbs | AB- | 32 | F | | |
| Betsy Drasdell | 452-22-8900 | 5'9" | 136 lbs | O- | 31 | F | | |
| Keith Drittle | 189-42-7890 | 5'7" | 151 lbs | A+ | 31 | M | | |

| Start | W Workbench | | | | | | | 12:42 PM 08/14/2012 |

*FIG. 13*

WORKBENCH FOR INTEGRATING APPLICATIONS

CROSS-REFERENCE TO RELATED APPLICATION

The present application is a U.S. nonprovisional patent application of, and claims priority under 35 U.S.C. § 119(e) to, U.S. provisional patent application Ser. No. 61/683,152, filed Aug. 14, 2012, which provisional patent application is hereby incorporated by reference herein.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
| --- | --- | --- |
| readme.txt | Aug. 14, 2012 18:06 | 2745 |
| ASCIFY.txt | Aug. 14, 2012 13:18 | 37473 |
| main-zip1.txt | Aug. 14, 2012 13:22 | 22478848 |
| main-zip2.txt | Aug. 14, 2012 13:22 | 22478848 |
| main-zip3.txt | Aug. 14, 2012 13:22 | 22478848 |
| main-zip4.txt | Aug. 14, 2012 13:22 | 22478848 |
| main-zip5.txt | Aug. 14, 2012 13:22 | 22478848 |
| main-zip6.txt | Aug. 14, 2012 13:22 | 22478848 |
| main-zip7.txt | Aug. 14, 2012 13:22 | 22478848 |
| main-zip8.txt | Aug. 14, 2012 13:22 | 8867045 |

One of these files, "readme.txt", contains instructions for extracting information from other of the files. These other files are compressed binary files that have been converted to ascii format. These files can be converted back to a compressed .zip archive utilizing an assembly conversion program source code for which is contained in "ascify.txt". The readme file includes instructions for compiling and running this conversion program, and instructions for converting the other text files to compressed, binary files, as well as instructions for recreating a directory structure for these compressed files.

Some of these compressed, binary files include source code written in C Sharp that can be compiled utilizing Microsoft Visual Studio 2008. The target environment for implementations utilizing such source code is 32-bit or 64-bit Windows XP, Vista, or 7.

BACKGROUND OF THE INVENTION

The use of software in business and other applications is ubiquitous today. This can include both brand new software and older software. Often, a single entity or organization will find itself using multiple pieces of software that may not be able to communicate with one another. In some events, an entity or organization may find itself using multiple pieces of software for the same or overlapping purposes. Further, sometimes, organizations merge or evolve and may find some of their data or infrastructure tied to particular software or systems, while other data or infrastructure is tied to other software or systems.

Further, organizations may find themselves tied to multiple systems. Conventionally, users need to log in and access each system separately. For example, typically, if a user wants to see data from multiple electronic healthcare record software applications at the same time (say to compare records for consistency), he or she typically has to close one UI, hold the target information in working memory, and open a second UI. This allows for errors, is time consuming, and can be very frustrating (especially since at least one of the interfaces would likely require a remote desktop/Citrix type solution to access).

Alternatively, the user could bring up both UIs at once in a dual monitor environment. This is also challenging since the data will often be presented to the user inconsistently. For example, the UIs may display data in different locations, the applications may user different units of measure, and design elements such as indicator icons could deviate from one another. This dual monitor environment could lead to frustration, errors, and patient safety issues.

Needs exists for improvement in facilitating the integration of software. These and other needs are addressed by one or more aspects of the present invention.

SUMMARY OF THE INVENTION

The present invention includes many aspects and features. Moreover, while many aspects and features relate to, and are described in, the context of electronic healthcare records, the present invention is not limited to use only in this context, as will become apparent from the following summaries and detailed descriptions of aspects, features, and one or more embodiments of the present invention.

Accordingly, one aspect of the present invention relates to a method comprising displaying, to a user via an electronic display associated with an electronic device, a login interface; receiving, from the user via one or more input devices associated with the electronic device, input corresponding to entry of first authentication credentials; authenticating, at a first authentication system associated with a first software application, the user utilizing the first authentication credentials; automatically looking up second authentication credentials stored in association with an account of the user, the second authentication credentials being associated with a second software application; automatically authenticating with a second authentication system associated with the second software application; automatically looking up third authentication credentials stored in association with an account of the user, the third authentication credentials being associated with a third software application; automatically authenticating with a third authentication system associated with the third software application; receiving, by the first software application, electronic healthcare record data from a first database associated with the second software application; receiving, by the first software application, electronic healthcare record data from a second database associated with the third software application; normalizing, by the first software application, data received from the first database and data received from the second database to be in the same format; and displaying, to the user via the electronic display in an interface of the first software application, electronic healthcare records corresponding to data received from both the first database and the second database, the displayed electronic healthcare records including information corresponding to at least some of the data that was normalized by the first software application.

In at least some implementations in accordance with one or more aspects, a method further includes receiving, from the user via one or more input devices associated with the electronic device, input corresponding to editing of a displayed electronic healthcare record; and effecting pushing, by the first software application, of data corresponding to the editing to the first and second databases.

In at least some implementations in accordance with one or more aspects, a method further includes receiving, from the user via one or more input devices associated with the electronic device, input corresponding to creation of a new electronic healthcare record; and effecting pushing, by the first software application, of data corresponding to the creation to the first and second databases.

In at least some implementations in accordance with one or more aspects, a method further includes receiving, from the user via one or more input devices associated with the electronic device, input corresponding to deletion of an electronic healthcare record; and effecting pushing, by the first software application, of data corresponding to the deletion to the first and second databases.

In at least some implementations in accordance with one or more aspects, the second application comprises an acute care application.

In at least some implementations in accordance with one or more aspects, the second application comprises an ambulatory care application.

In at least some implementations in accordance with one or more aspects, the second application comprises an enterprise electronic healthcare record application.

In at least some implementations in accordance with one or more aspects, the electronic device comprises a desktop.

In at least some implementations in accordance with one or more aspects, the electronic device comprises a laptop.

In at least some implementations in accordance with one or more aspects, the electronic device comprises a smartphone.

In at least some implementations in accordance with one or more aspects, the electronic device comprises a phone.

In at least some implementations in accordance with one or more aspects, the electronic device comprises a tablet.

In at least some implementations in accordance with one or more aspects, the electronic display comprises a touchscreen.

In at least some implementations in accordance with one or more aspects, the electronic display comprises a monitor.

In at least some implementations in accordance with one or more aspects, the one or more input devices comprise a mouse.

In at least some implementations in accordance with one or more aspects, the one or more input devices comprise a keyboard.

In at least some implementations in accordance with one or more aspects, the one or more input devices comprise a mouse and keyboard.

In at least some implementations in accordance with one or more aspects, the one or more input devices comprise a touchscreen.

In at least some implementations in accordance with one or more aspects, the electronic display comprises a touchscreen, and wherein the one or more input devices comprise the touchscreen.

Another aspect relates to a method comprising displaying, to a user via an electronic display associated with an electronic device, a login interface; receiving, from the user via one or more input devices associated with the electronic device, input corresponding to entry of first authentication credentials; authenticating, at a first authentication system associated with a first software application, the user utilizing the first authentication credentials; receiving, by the first software application, electronic healthcare record data from a first database associated with a first electronic healthcare record application; receiving, by the first software application, electronic healthcare record data from a second database associated with a second electronic healthcare record application; normalizing, by the first software application, data received from the first database and data received from the second database to be in the same format; and displaying, to the user via the electronic display in an interface of the first software application, electronic healthcare records corresponding to data received from both the first database and the second database, the displayed electronic healthcare records including information corresponding to at least some of the data that was normalized by the first software application.

In at least some implementations in accordance with one or more aspects, a method further includes receiving, from the user via one or more input devices associated with the electronic device, input corresponding to editing of a displayed electronic healthcare record; and effecting pushing, by the first software application, of data corresponding to the editing to the first and second databases.

In at least some implementations in accordance with one or more aspects, a method further includes receiving, from the user via one or more input devices associated with the electronic device, input corresponding to creation of a new electronic healthcare record; and effecting pushing, by the first software application, of data corresponding to the creation to the first and second databases.

In at least some implementations in accordance with one or more aspects, a method further includes receiving, from the user via one or more input devices associated with the electronic device, input corresponding to deletion of an electronic healthcare record; and effecting pushing, by the first software application, of data corresponding to the deletion to the first and second databases.

In at least some implementations in accordance with one or more aspects, the first electronic healthcare record application comprises an acute care application.

In at least some implementations in accordance with one or more aspects, the first electronic healthcare record application comprises an ambulatory care application.

In at least some implementations in accordance with one or more aspects, the first electronic healthcare record application comprises an enterprise electronic healthcare record application.

Another aspect relates to a method comprising displaying, to a user via an electronic display associated with an electronic device, a login interface; receiving, from the user via one or more input devices associated with the electronic device, input corresponding to entry of first authentication credentials; authenticating, at a first authentication system associated with a first software application, the user utilizing the first authentication credentials; receiving, by the first software application, electronic healthcare record data from a first database associated with a first electronic healthcare record application; receiving, by the first software application, electronic healthcare record data from a second database associated with a second electronic healthcare record application; displaying, to the user via the electronic display in an interface of the first software application, electronic healthcare records corresponding to data received from both the first database and the second database; receiving, from the user via one or more input devices associated with the electronic device, input corresponding to editing of a displayed electronic healthcare record; and effecting pushing, by the first software application, of data corresponding to the editing to the first and second databases.

In at least some implementations in accordance with one or more aspects, the first electronic healthcare record application comprises an acute care application.

In at least some implementations in accordance with one or more aspects, the first electronic healthcare record application comprises an ambulatory care application.

In at least some implementations in accordance with one or more aspects, the first electronic healthcare record application comprises an enterprise electronic healthcare record application.

Another aspect relates to a method comprising displaying, to a user via an electronic display associated with an electronic device, a login interface; receiving, from the user via one or more input devices associated with the electronic device, input corresponding to entry of first authentication credentials; authenticating, at a first authentication system associated with a first software application, the user utilizing the first authentication credentials; receiving, by the first software application, electronic healthcare record data from a first database associated with a first electronic healthcare record application; receiving, by the first software application, electronic healthcare record data from a second database associated with a second electronic healthcare record application; displaying, to the user via the electronic display in an interface of the first software application, electronic healthcare records corresponding to data received from both the first database and the second database; receiving, from the user via one or more input devices associated with the electronic device, input corresponding to creation of a new electronic healthcare record; and effecting pushing, by the first software application, of data corresponding to the creation to the first and second databases.

Another aspect relates to a method comprising displaying, to a user via an electronic display associated with an electronic device, a login interface; receiving, from the user via one or more input devices associated with the electronic device, input corresponding to entry of first authentication credentials; authenticating, at a first authentication system associated with a first software application, the user utilizing the first authentication credentials; receiving, by the first software application, electronic healthcare record data from a first database associated with a first electronic healthcare record application; receiving, by the first software application, electronic healthcare record data from a second database associated with a second electronic healthcare record application; displaying, to the user via the electronic display in an interface of the first software application, electronic healthcare records corresponding to data received from both the first database and the second database; receiving, from the user via one or more input devices associated with the electronic device, input corresponding to deletion of an electronic healthcare record; and effecting pushing, by the first software application, of data corresponding to the deletion to the first and second databases.

Another aspect relates to software in which data from various disparate applications or interfaces is combined into a single HTML view via panels developed specifically for use in workbench with the new combined data.

Another aspect relates to a workbench application which provides fast and easy access to information stored in multiple database applications.

Another aspect relates to a workbench application which provides the ability to record new data that is then pushed out to disparate applications (opposed to entering the same data multiple times in a single access environment).

Another aspect relates to a workbench application which provides more unified design elements across products leading to greater perception of quality.

Another aspect relates to a workbench application which provides new workflows that can accomplish all workflow related tasks within the workbench environment (as opposed to jumping back and forth between different applications for a single workflow).

Another aspect relates to a workbench application which provides an integrated view of patient data, leading to less potential error (due to translating between disparate UIs) and greater diagnostic capabilities.

Another aspect relates to a workbench application which provides a single sign in for multiple database applications.

Another aspect relates to a workbench application which provides the capability for fast and inexpensive integration of third party technology through the distribution of a Workbench SDK.

Another aspect relates to a workbench application in which data from multiple EMR applications is displayed in a single GUI.

Another aspect relates to a workbench application in which data from multiple applications or databases is normalized and presented in new, merged panels.

Another aspect relates to a workbench application which provides an Open SDK that allows for third party development of complementary software.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein, FIG. 1 schematically illustrates how a workbench application in accordance with one or more preferred implementations is configured for the retrieval of data from two or more applications or databases;

FIGS. 3-4 illustrate an acute care application;

FIGS. 5-6 illustrate an ambulatory care application;

FIGS. 12-13 illustrates an exemplary interface for a workbench application; and

DETAILED DESCRIPTION

Figure 1:
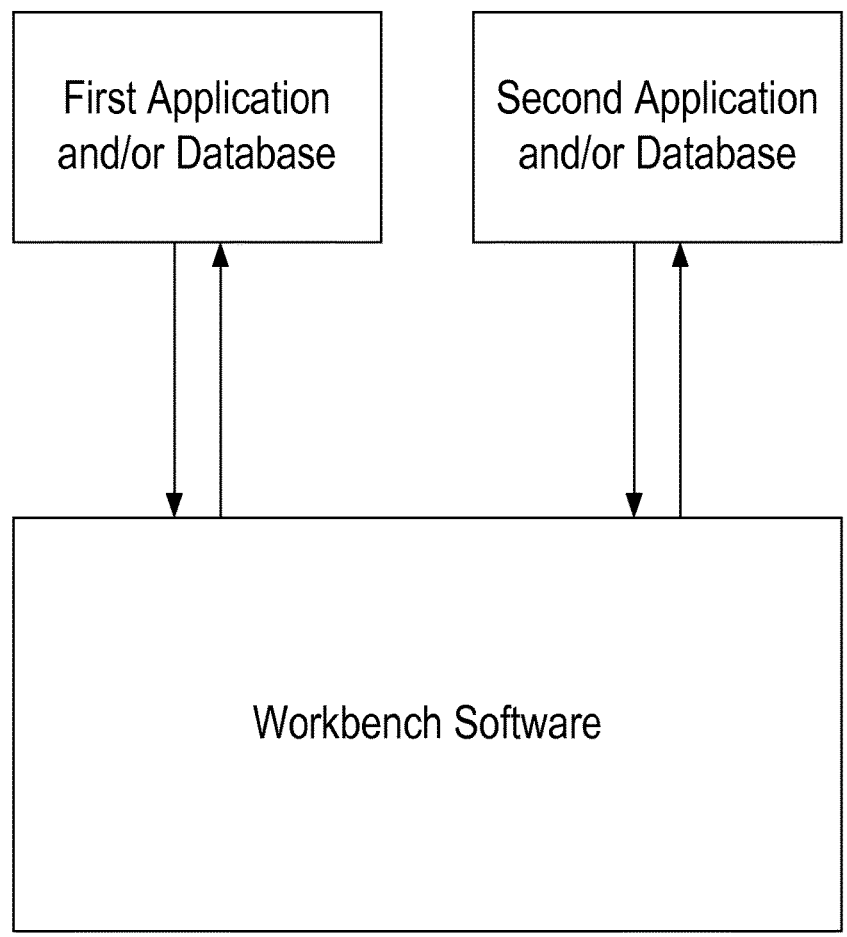

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with a preferred embodiment, software is configured to interface with multiple other disparate software applications or databases to present a single user interface to a user which allows the user to view and modify data from multiple applications and/or databases without having to worry about which application the data comes from. In one or more preferred implementations, the software provides a user interface which presents to the user seamless integration of data from multiple disparate applications/databases, even though behind-the-scenes the software may have to continually interface with one or both applications to retrieve, modify, and store data. The software preferably allows for easy retrieval and presentation of data from two or more applications and/or databases together, and subsequent storage of all data in the appropriate application/database, as schematically illustrated in FIG. 1.

Figure 2:
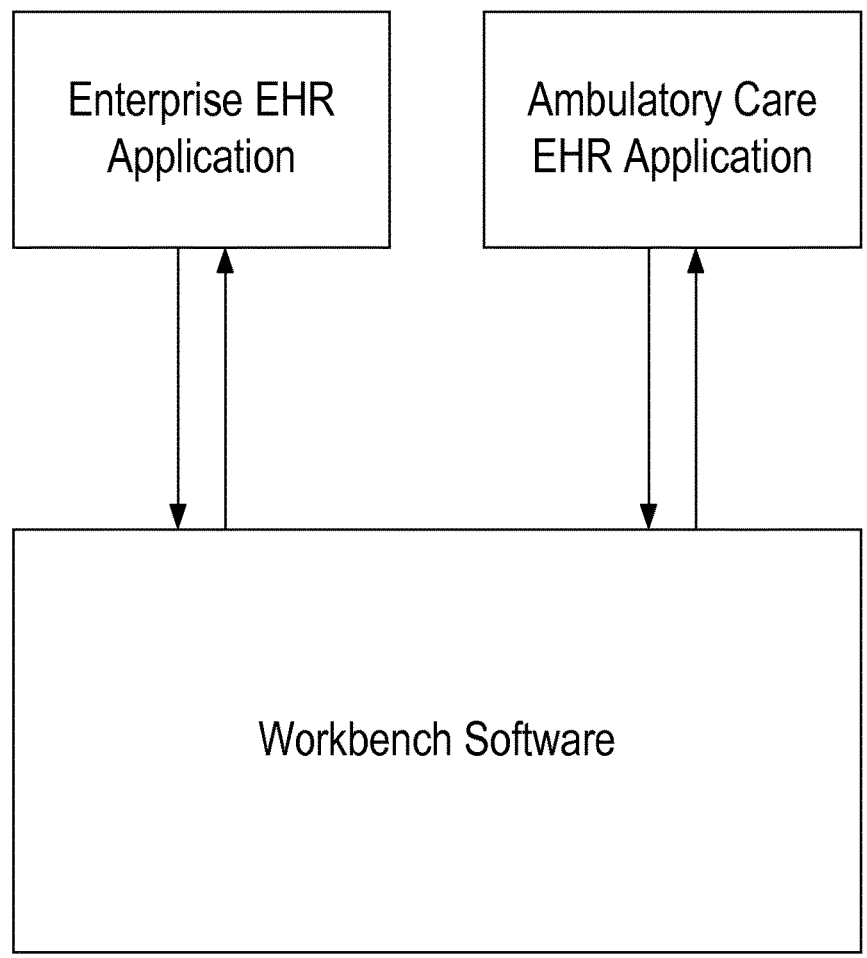
FIG. 2 schematically illustrates interaction of an exemplary workbench application with an enterprise EHR application and an ambulatory care EHR application.

In one or more preferred implementations, exemplary such software comprises workbench software configured to integrate multiple EHR/EMR applications and allow for retrieval, presentation, creation, editing, and updating of data from such EHR/EMR applications. For example, in one preferred implementation, such software facilitates integration of a small scale solution, or e.g. an ambulatory care solution, and an enterprise scale solution, as schematically illustrated in FIG. 2. Such a software workbench is believed, for example, to allow a user or organization utilizing a small scale solution or an ambulatory care solution to leverage data from an enterprise scale solution, such as, for example, an enterprise scale solution of an associated organization or entity.

In one or more preferred implementations workbench software includes a web interface configured to allow a user to access, modify, and save data from multiple disparate applications.

In one or more preferred implementations, workbench software can be characterized as serving an abstraction function in seamlessly interfacing with various applications while presenting a unitary interface to a user who may be unaware that the data they are viewing/modifying is derived from multiple/disparate applications.

One or more preferred implementations provide a software architecture and interface that allows healthcare professionals to read, write, and understand data from disparate data sources within a single user interface. This interface requires only a single login for the user to access various healthcare and communication applications that would otherwise require opening individually with various security credentials. Having logged into the workbench, the user is able to view data from multiple database applications (EMRs) and view all information as a single, integrated patient record.

Preferably, a single security agent provides to users the ability to use a single set of security credentials (e.g. a user name and password) to access data from multiple healthcare and non-healthcare applications, such as, for example, acute care EMRs (electronic medical records), ambulatory EMRs, office/hospital financial and administrative software programs, and third party applications such as instant messaging and other communications/ecommerce applications that are developed within the confines of a proprietary Software Development Kit (SDK) that is defined by the Workbench model.

Figure 3:
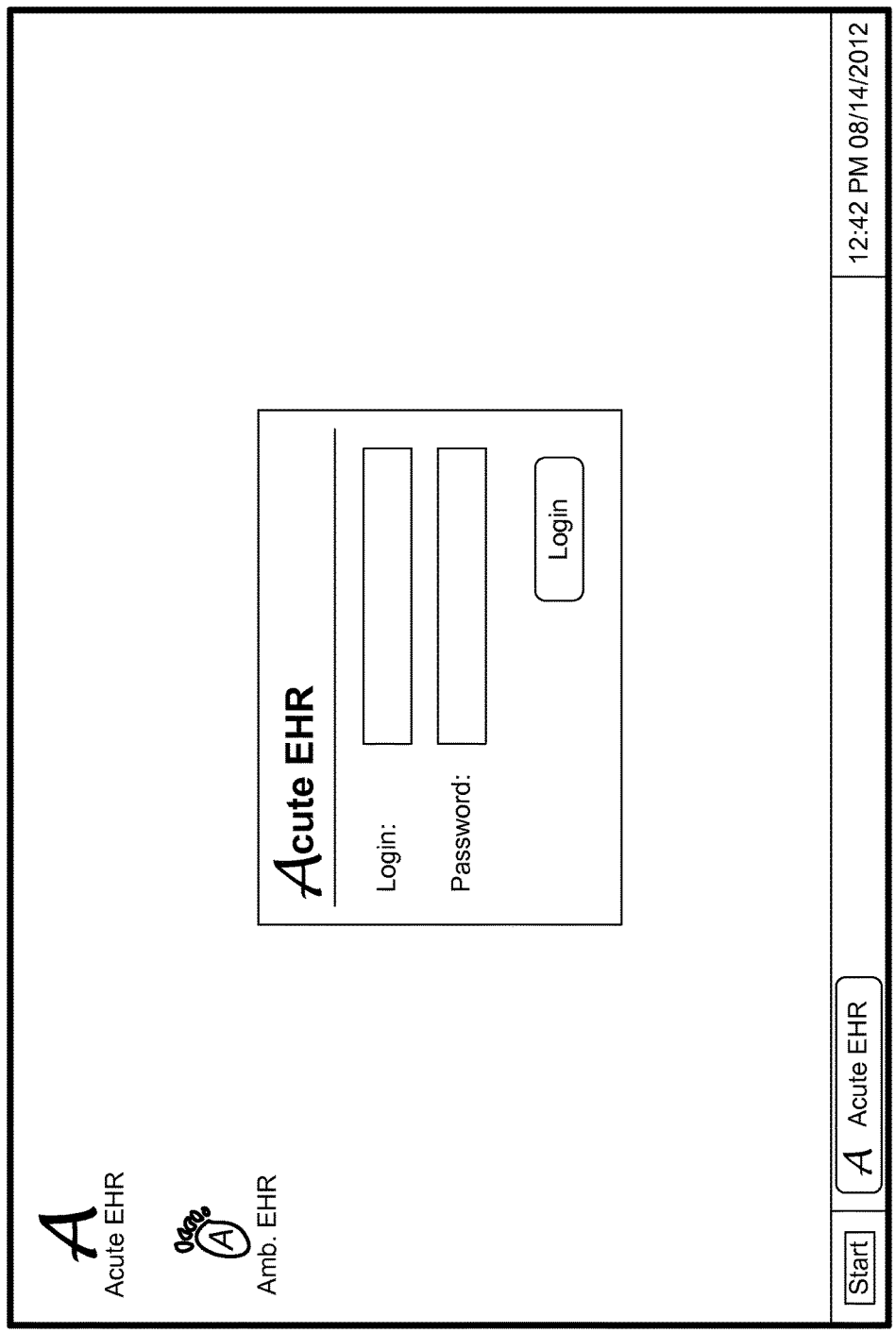
Figure 5:
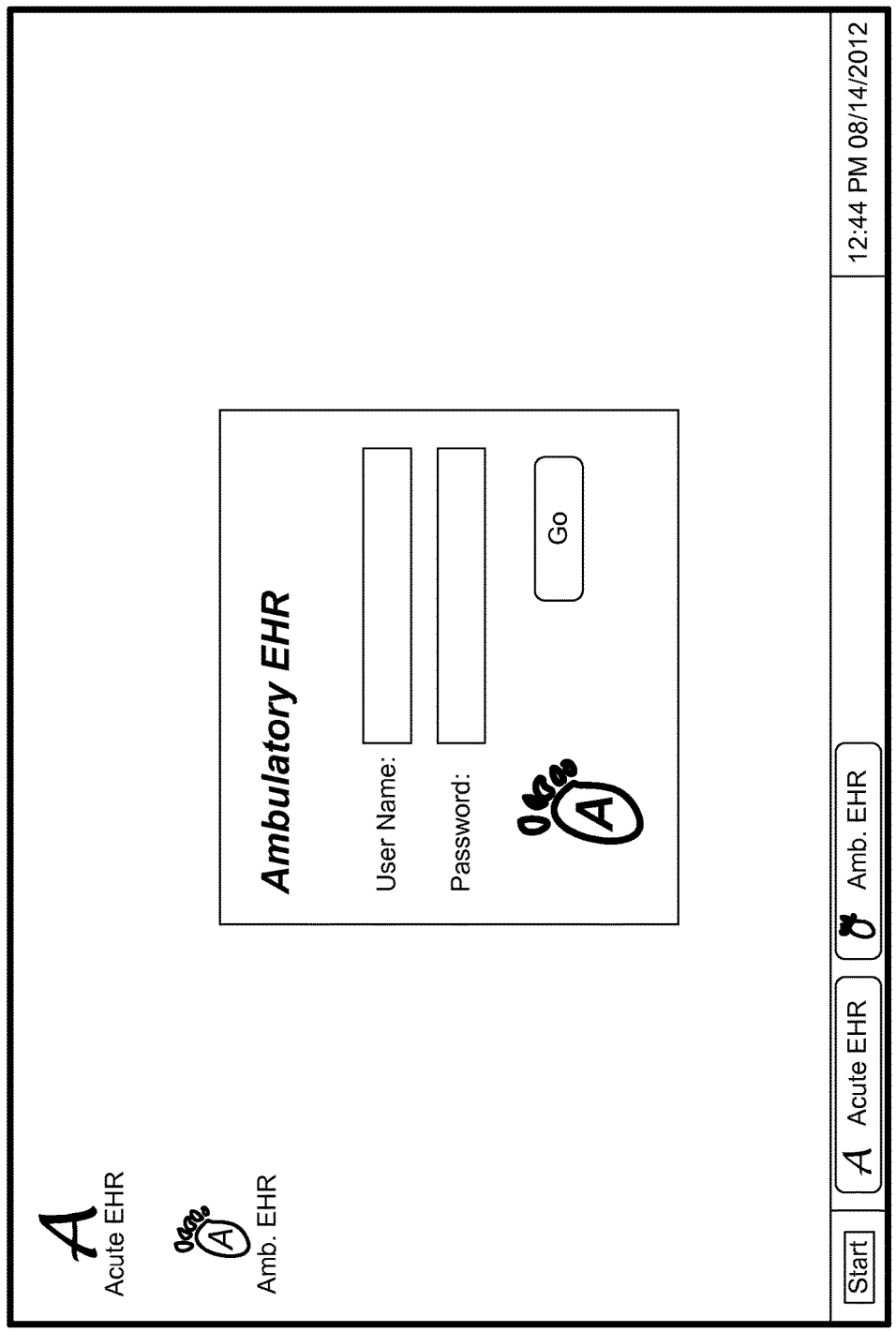

This is in contrast to conventional methodologies which typically require multiple logins to access multiple different applications or data from such applications. For example, FIG. 3 illustrates a conventional login interface for a first application. In the illustrated example, it is a login interface for an acute care EMR application. Upon logging in, a user can access records stored in the acute care EMR application, as illustrated in FIG. 4. If, however, the user decides they also want to access records stored in an ambulatory care EMR application, they would conventionally need to separately log in to that application, as illustrated in FIG. 5. Only after separately logging in could the user then also access data from the ambulatory care EMR application, as illustrated in FIG. 6.

Figure 7:
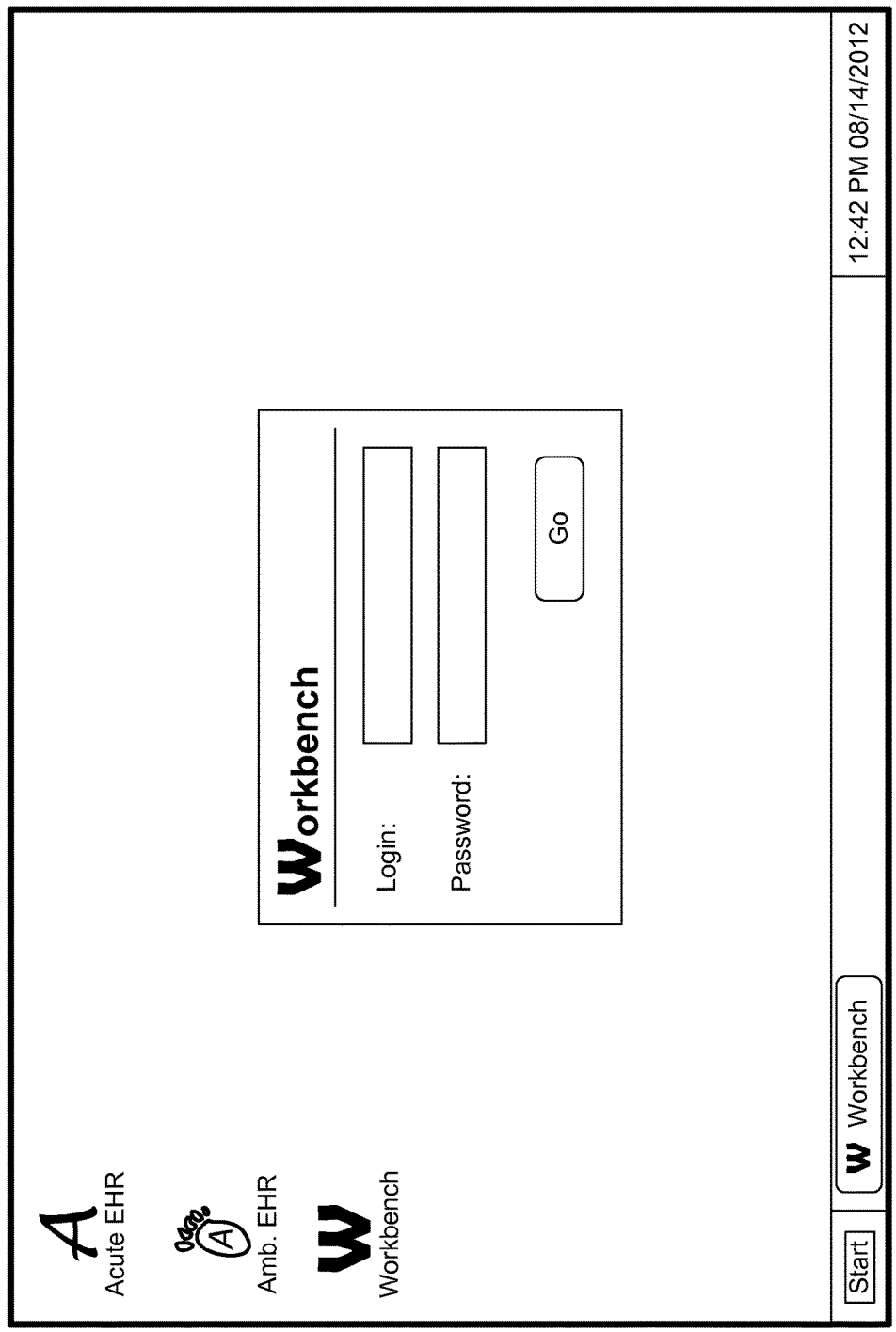
FIG. 7 illustrates an exemplary login interface for a workbench application in accordance with one or more preferred implementations.
Figure 8:
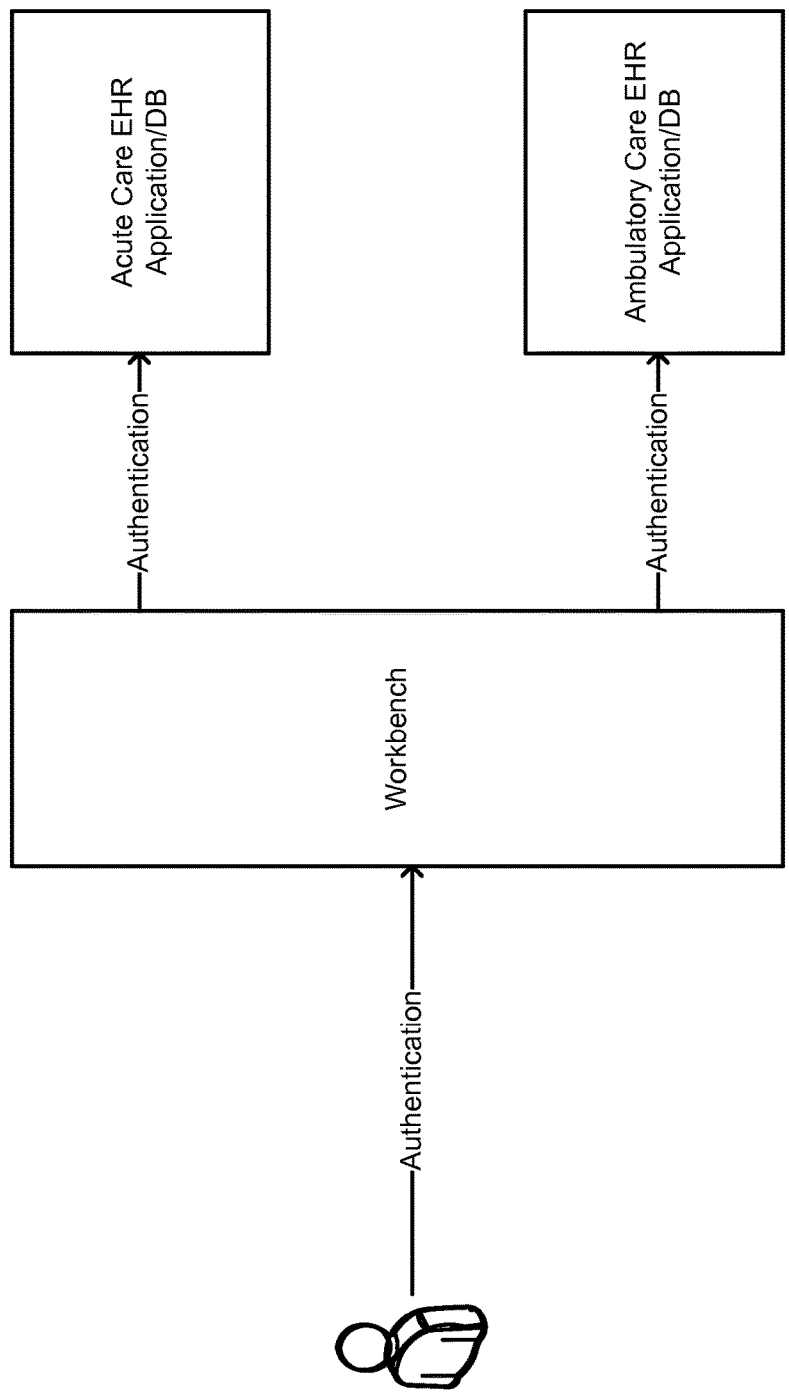
FIG. 8 schematically illustrates an exemplary process whereby a user authenticates with a workbench application which in turn authenticates with other, disparate applications or databases.

FIG. 7 illustrates an exemplary login interface for a workbench application in accordance with one or more preferred implementations. After logging in once to the workbench application, security credentials associated with that user can be utilized to authenticate with other, disparate applications, such as the exemplary applications illustrated in FIGS. 3-6. FIG. 8 schematically illustrates an exemplary such process, where a user authenticates with a workbench application which in turn authenticates with other, disparate applications or databases.

Figure 9:
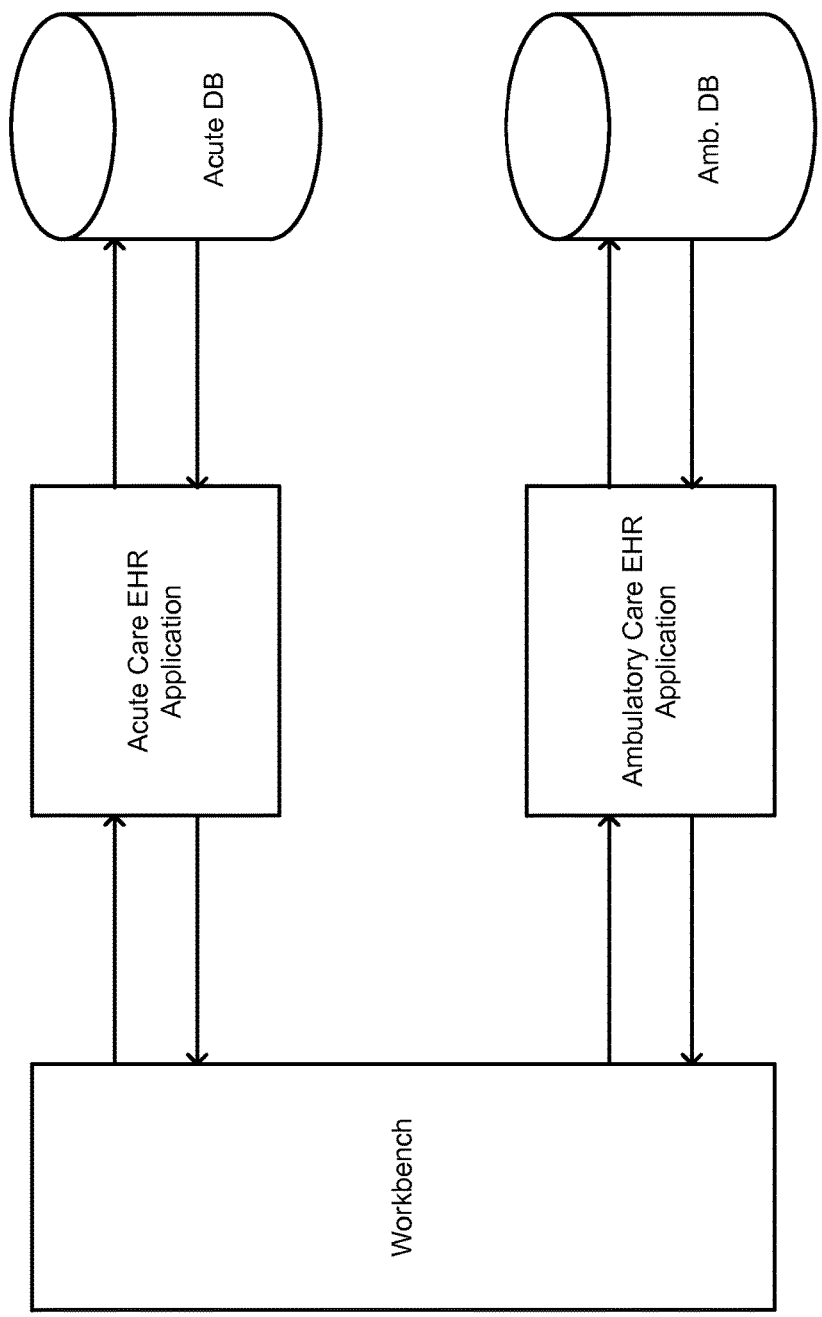
FIG. 9 illustrates a schematic of an exemplary implementation in which a workbench application communicates with several other applications, which other applications in turn each request and receive data from a respective database and communicate such data to the workbench application.
Figure 10:
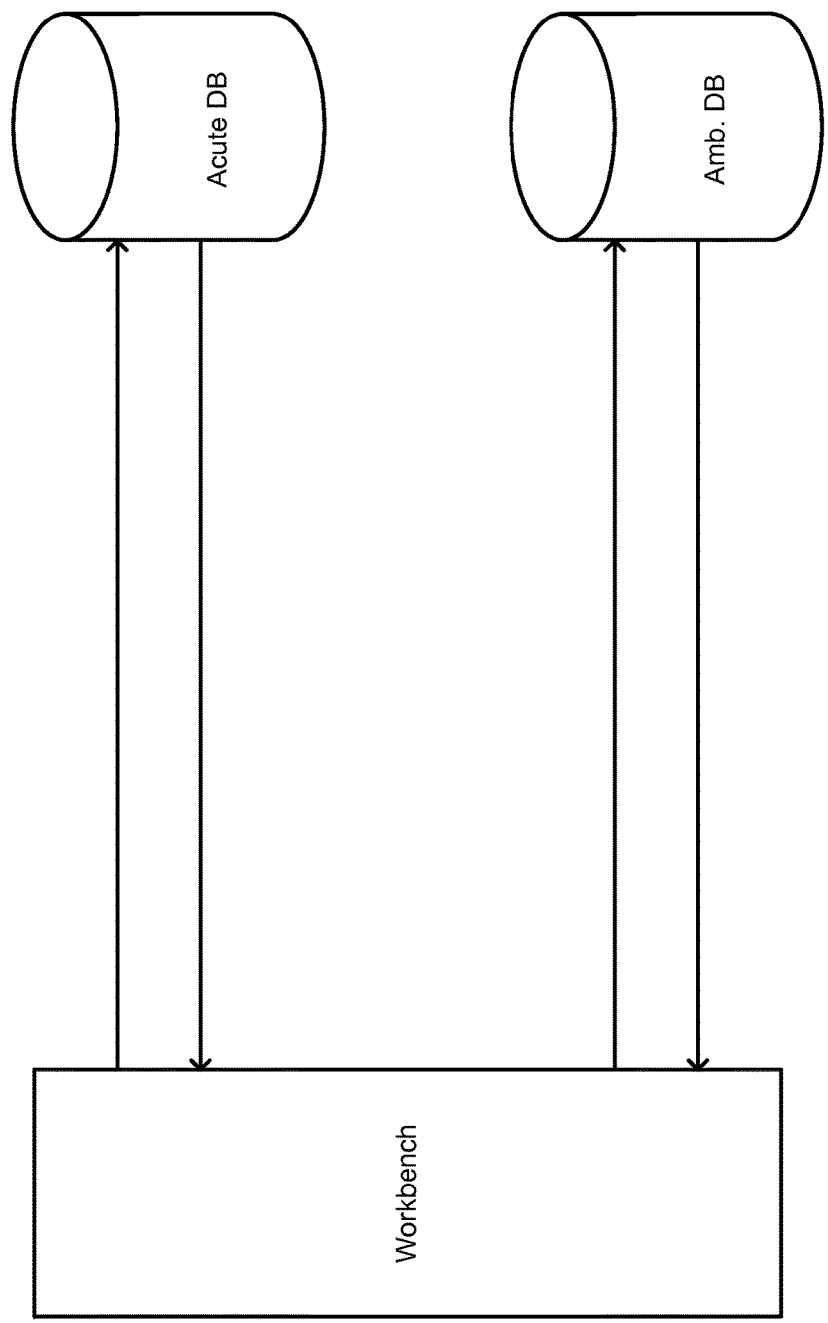
FIG. 10 illustrates a schematic of an exemplary implementation in which a workbench application communicates with several databases directly.
Figure 11:
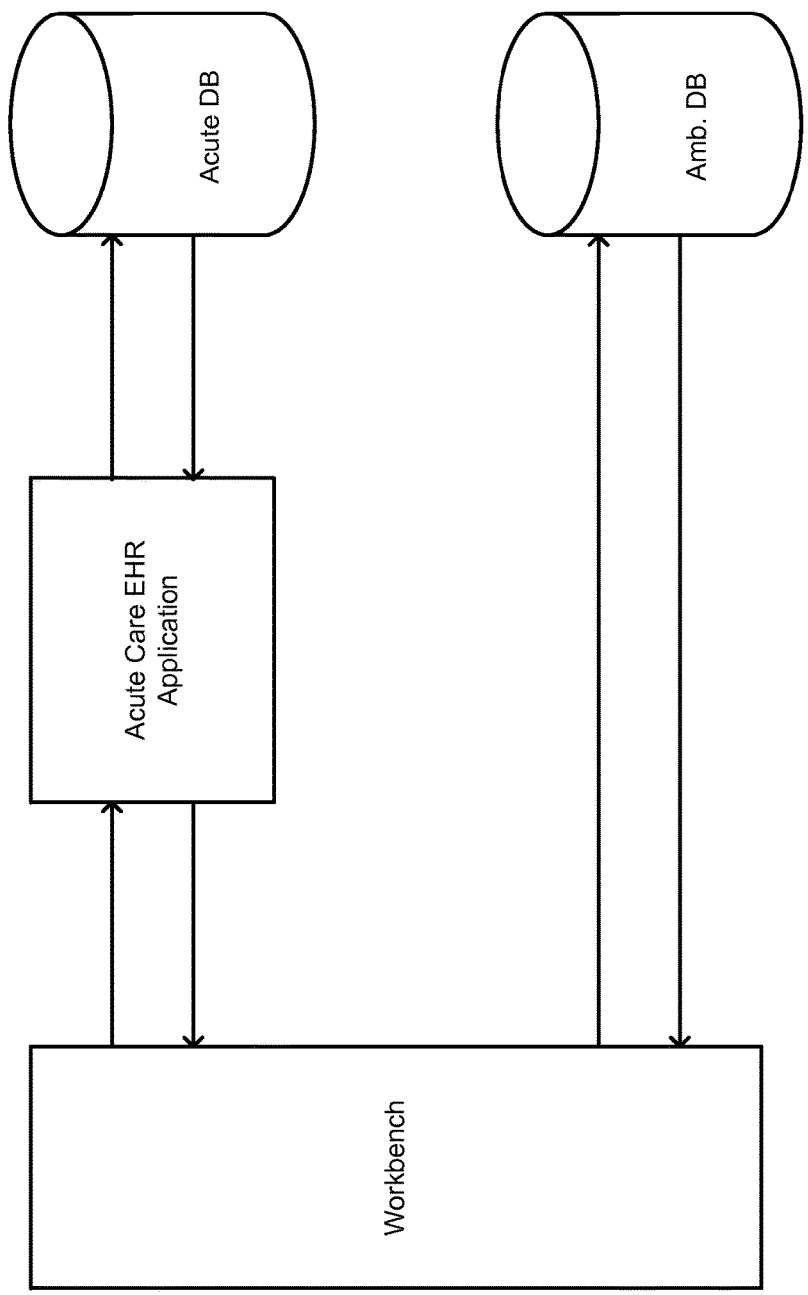
FIG. 11 illustrates a schematic of an exemplary implementation in which a workbench application communicates with an application and a database.

Thereafter, data is loaded from each disparate application or database. FIG. 9 illustrates a schematic of an exemplary implementation in which a workbench application communicates with several other applications (e.g. via an API), which other applications in turn each request and receive data from a respective database and communicate such data to the workbench application. Alternatively, in at least some implementations, a workbench application may communicate with one or more databases directly, as illustrated in FIG. 10. In at least some implementations, a workbench application may communicate with some applications and some databases, as illustrated in FIG. 11.

In any event, in one or more preferred implementations a workbench application is configured to load data from other disparate applications. FIG. 12 illustrates an exemplary interface for such a workbench application displaying data loaded from the applications previously illustrated in FIGS. 3-6.

Preferably, when a user logs into a workbench application, they may be able to see a patient records that contain information from multiple applications, e.g. information from both ambulatory and acute care EMRs.

In one or more preferred implementations, a workbench application includes data "normalization" functionality for translating and sharing data between disparate applications, regardless of whether such applications utilize identical data formats. For example, in one or more preferred implementations, while data may be formatted differently in individual EMR applications, a workbench application will take data from multiple applications and present it in a single, consistent user interface. FIG. 12 illustrates a generalized example of this where data from a first application/database listing height in feet and inches and data from a second application/database listing height in inches has been normalized for display in a workbench application in feet and inches.

Figure 14:
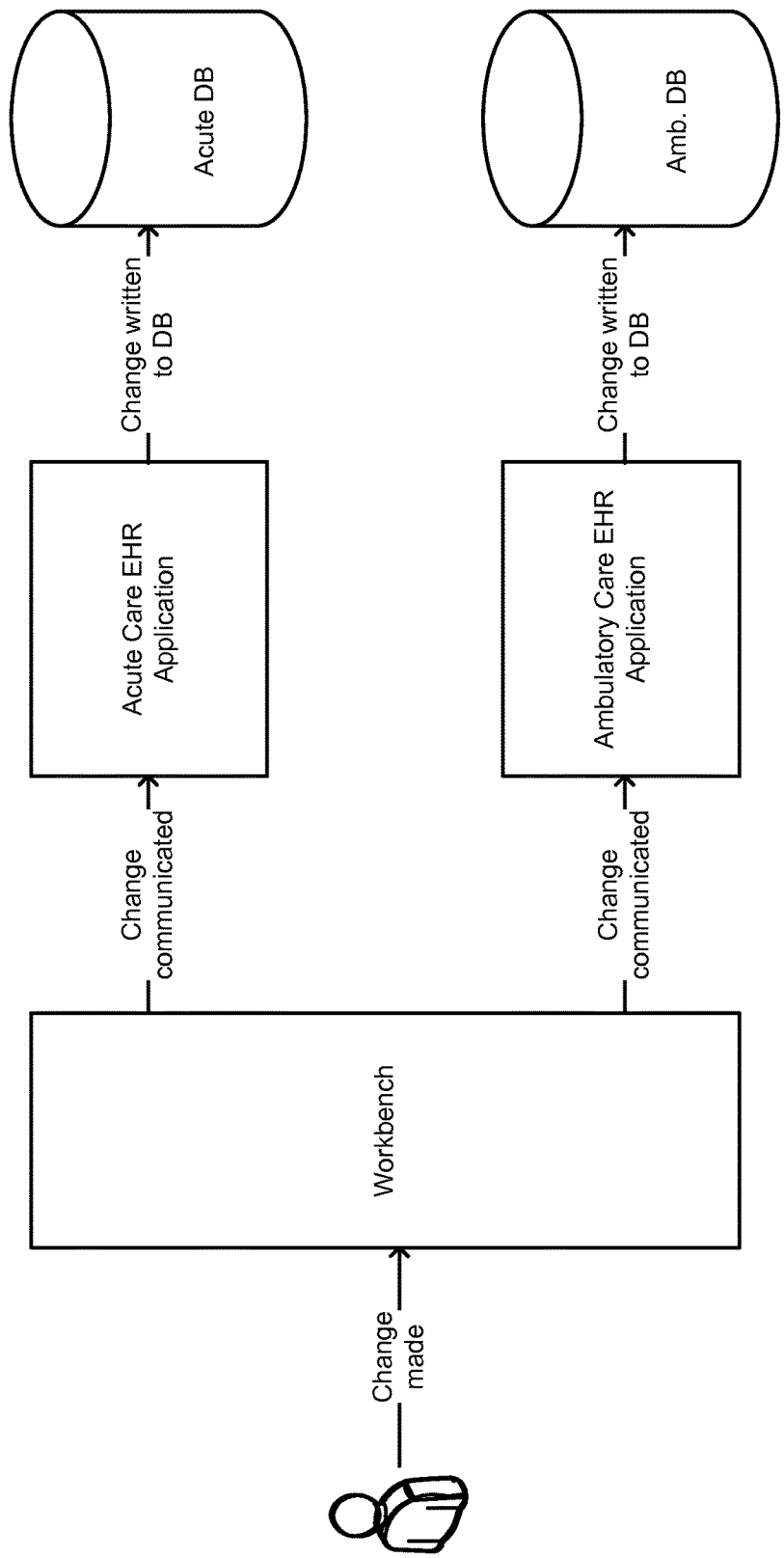
FIG. 14 illustrates pushing of an edit made in a workbench application to multiple, disparate databases.

In one or more preferred implementations, new records, data, changes, or edits are pushed out to multiple, disparate applications or databases allowing a user to create/input/edit an item once, rather than multiple times in multiple applications. For example, returning to the example of FIG. 12, if a user determines that John Doe's weight should actually be 181 pounds rather than 175 pounds, the user could edit this value via the workbench application, as illustrated in FIG. 13, and such edit could be pushed to databases for multiple, disparate applications, as illustrated in FIG. 14.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for allowing a healthcare practitioner to assimilate, review, and compare patient data from two different electronic healthcare record (EHR) software applications via a web application, the method comprising:
 (a) displaying, to a user via an electronic display associated with an electronic device, a login interface of a web application;

(b) receiving, at the login interface from the user via one or more input devices associated with the electronic device, input corresponding to entry of first authentication credentials;

(c) authenticating, at a first authentication system associated with the web application, the user utilizing the first authentication credentials;

(d) automatically looking up second authentication credentials stored in association with an account of the user, the second authentication credentials being associated with a first EHR software application;

(e) automatically authenticating, by the web application with a running instance of the first EHR software application;

(f) automatically looking up third authentication credentials stored in association with an account of the user, the third authentication credentials being associated with a second EHR software application;

(g) automatically authenticating, by the web application, with a running instance of the second EHR software application;

(h) receiving, by the web application, electronic healthcare record data from the first EHR software application;

(i) receiving, by the web application, electronic healthcare record data from the second EHR software application;

(j) normalizing, by the web application, data received from the first EHR software application and data received from the second EHR software application to be in the same format; and (k) displaying, to the user via the electronic display in a web interface of the web application, first electronic healthcare data corresponding to data received from both the first EHR software application and the second EHR software application, the displayed electronic healthcare data including information corresponding to at least some of the data that was normalized by the web application;

(l) receiving, from the user via one or more input devices associated with the electronic device, input corresponding to editing of a first data item associated with a particular patient forming part of the first electronic healthcare data displayed in the web interface of the web application;

(m) automatically communicating, by the web application, an indication of the editing of the first data item to the first EHR software application for updating of corresponding data for the particular patient in the first EHR software application;

(n) automatically communicating, by the web application, an indication of the editing of the first data item to the second EHR software application for updating of corresponding data for the particular patient in the second EHR software application;

(o) receiving, at the web interface from the user via one or more input devices associated with the electronic device, input corresponding to engagement with one or more interface elements of the web interface;

(p) in response to the receipt of input corresponding to engagement with one or more interface elements, (i) effecting navigation, by the web application utilizing context information from the web application in the form of an indication of the particular patient, of the first EHR software application to a native interface of the first EHR software application displaying patient data for the particular patient, (ii) displaying, within a first frame of the web application, the native interface of the first EHR software application, and (iii) effecting navigation, by the web application utilizing context information from the web application in the form of an indication of the particular patient, of the second EHR software application to a native interface of the second EHR software application displaying patient data for the particular patient, (iv) displaying, within a second frame of the web application, the native second interface of the second EHR software application, (v) wherein the native interface for the first EHR software application displayed within the first frame of the web application and the native interface for the second EHR software application displayed within the second frame of the web application both reflect the edit made to the first data item in the web interface of the web application.

2. The method of claim 1, wherein the first EHR software application comprises an acute care application.

3. The method of claim 1, wherein the first EHR software application comprises an ambulatory care application.

4. The method of claim 1, wherein the first EHR software application comprises an enterprise electronic healthcare record application.

5. The method of claim 1, wherein the electronic device comprises a desktop, a laptop, a smartphone, a phone or a tablet.

6. The method of claim 1, wherein the electronic display comprises a touchscreen.

7. A method for allowing a healthcare practitioner to assimilate, review, and compare patient data from two different electronic healthcare record (EHR) software applications via a web application, the method comprising:

(a) displaying, to a user via an electronic display associated with an electronic device, a login interface of a web application;

(b) receiving, at the login interface from the user via one or more input devices associated with the electronic device, input corresponding to entry of first authentication credentials;

(c) authenticating, at a first authentication system associated with the web application, the user utilizing the first authentication credentials;

(d) automatically looking up second authentication credentials stored in association with an account of the user, the second authentication credentials being associated with a first EHR software application;

(e) automatically authenticating, by the web application with a running instance of the first EHR software application;

(f) automatically looking up third authentication credentials stored in association with an account of the user, the third authentication credentials being associated with a second EHR software application;

(g) automatically authenticating, by the web application, with a running instance of the second EHR software application;

(h) receiving, by the web application, electronic healthcare record data from the first EHR software application;

(i) receiving, by the web application, electronic healthcare record data from the second EHR software application;

(j) normalizing, by the web application, data received from the first EHR software application and data received from the second EHR software application to be in the same format; and (k) displaying, to the user via the electronic display in a web interface of the web application, first electronic healthcare data corresponding to data received from both the first EHR software application and the second EHR software application, the displayed electronic healthcare data including information corresponding to at least some of the data that was normalized by the web application;

(l) receiving, from the user via one or more input devices associated with the electronic device, input corresponding to entry of a new data item associated with a particular patient via the web interface of the web application;

(m) automatically communicating, by the web application, an indication of the entry of the new data item to the first EHR software application for updating of corresponding data for the particular patient in the first EHR software application;

(n) automatically communicating, by the web application, an indication of the entry of the new data item to the second EHR software application for updating of corresponding data for the particular patient in the second EHR software application;

(o) receiving, at the web interface from the user via one or more input devices associated with the electronic device, input corresponding to engagement with one or more interface elements of the web interface;

(p) in response to the receipt of input corresponding to engagement with one or more interface elements,
  (i) effecting navigation, by the web application utilizing context information from the web application in the form of an indication of the particular patient, of the first EHR software application to a native interface of the first EHR software application displaying patient data for the particular patient,
  (ii) displaying, within a first frame of the web application, the native interface of the first EHR software application, and
  (iii) effecting navigation, by the web application utilizing context information from the web application in the form of an indication of the particular patient, of the second EHR software application to a native interface of the second EHR software application displaying patient data for the particular patient,
  (iv) displaying, within a second frame of the web application, the native second interface of the second EHR software application,
  (v) wherein the native interface for the first EHR software application displayed within the first frame of the web application and the native interface for the second EHR software application displayed within the second frame of the web application both reflect the entry of the new data item via the web interface of the web application.

8. The method of claim 7, wherein the second application comprises an acute care application.

9. The method of claim 7, wherein the second application comprises an ambulatory care application.

10. The method of claim 7, wherein the second application comprises an enterprise electronic healthcare record application.

11. The method of claim 7, wherein the electronic device comprises a desktop.

12. The method of claim 7, wherein the electronic device comprises a laptop.

13. The method of claim 7, wherein the electronic device comprises a smartphone.

14. The method of claim 7, wherein the electronic device comprises a tablet.

15. The method of claim 7, wherein the electronic display comprises a touchscreen.

16. A method for allowing a healthcare practitioner to assimilate, review, and compare patient data from two different electronic healthcare record (EHR) software applications via a web application, the method comprising:

(a) displaying, to a user via an electronic display associated with an electronic device, a login interface of a web application;

(b) receiving, at the login interface from the user via one or more input devices associated with the electronic device, input corresponding to entry of first authentication credentials;

(c) authenticating, at a first authentication system associated with the web application, the user utilizing the first authentication credentials;

(d) automatically looking up second authentication credentials stored in association with an account of the user, the second authentication credentials being associated with a first EHR software application;

(e) automatically authenticating, by the web application with a running instance of the first EHR software application;

(f) automatically looking up third authentication credentials stored in association with an account of the user, the third authentication credentials being associated with a second EHR software application;

(g) automatically authenticating, by the web application, with a running instance of the second EHR software application;

(h) receiving, by the web application, electronic healthcare record data from the first EHR software application;

(i) receiving, by the web application, electronic healthcare record data from the second EHR software application;

(j) normalizing, by the web application, data received from the first EHR software application and data received from the second EHR software application to be in the same format; and (k) displaying, to the user via the electronic display in a web interface of the web application, first electronic healthcare data corresponding to data received from both the first EHR software application and the second EHR software application, the displayed electronic healthcare data including information corresponding to at least some of the data that was normalized by the web application;

(l) receiving, at the web interface from the user via one or more input devices associated with the electronic device, input corresponding to engagement with one or more interface elements of the web interface associated with a particular patient;

(m) in response to the receipt of input corresponding to engagement with one or more interface elements associated with the particular patient,
  (i) effecting navigation, by the web application utilizing context information from the web application in the form of an indication of the particular patient, of the first EHR software application to a native interface of the first EHR software application displaying patient data for the particular patient,
  (ii) displaying, within a first frame of the web application, the native interface of the first HER software application; (n) receiving, from the user via one or more input devices associated with the electronic device, input corresponding to editing of displayed electronic healthcare data; (o) effecting pushing, by the web application, of data corresponding to the editing to the first and second EHR software applications.

17. The method of claim 16, wherein the method further includes
   (a) receiving, from the user via one or more input devices associated with the electronic device, input corresponding to creation of a new electronic healthcare record;
   (b) effecting pushing, by the web application, of data corresponding to the creation to the first and second EHR software applications.

18. The method of claim 16, wherein the method further includes
   (a) receiving, from the user via one or more input devices associated with the electronic device, input corresponding to deletion of an electronic healthcare record;
   (b) effecting pushing, by the web application, of data corresponding to the deletion to the first and second EHR software applications.

19. The method of claim 16, wherein the electronic display comprises a touchscreen.

* * * * *